United States Patent
Mickley

Patent Number: 6,056,719
Date of Patent: May 2, 2000

[54] CONVERTIBLE CATHETER INCORPORATING A COLLAPSIBLE LUMEN

[75] Inventor: Timothy J. Mickley, Elk River, Minn.

[73] Assignee: SciMed Life Systems, Inc., Maple Grove, Minn.

[21] Appl. No.: 09/034,459

[22] Filed: Mar. 4, 1998

[51] Int. Cl.⁷ ............... A61M 29/00; A61M 25/00
[52] U.S. Cl. .................. 604/96; 604/96; 604/280
[58] Field of Search ............. 604/96, 282, 280, 604/160, 161, 281, 915, 921, 102; 606/192, 194; 600/585

[56] References Cited

U.S. PATENT DOCUMENTS

| | | | |
|---|---|---|---|
| 3,834,394 | 9/1974 | Hunter et al. | 128/325 |
| 4,295,464 | 10/1981 | Shihata | 128/1 R |
| 4,406,656 | 9/1983 | Hattler et al. | 604/280 |
| 4,490,421 | 12/1984 | Levy | 428/35 |
| 4,576,142 | 3/1986 | Schiff | 128/1 D |
| 4,601,713 | 7/1986 | Fuqua | 604/280 |
| 4,644,936 | 2/1987 | Schiff | 128/1 D |
| 4,697,573 | 10/1987 | Schiff | 128/1 D |
| 4,710,181 | 12/1987 | Fuqua | 604/280 |
| 4,738,666 | 4/1988 | Fuqua | 604/280 |
| 4,762,129 | 8/1988 | Bonzel | 128/344 |
| 4,798,193 | 1/1989 | Giesy et al. | 128/7 |
| 4,820,349 | 4/1989 | Saab | 128/344 |
| 4,881,547 | 11/1989 | Danforth | 128/344 |
| 4,909,252 | 3/1990 | Goldberger | 606/194 |
| 4,944,745 | 7/1990 | Sogard et al. | 606/194 |
| 4,958,634 | 9/1990 | Jang | 606/194 |
| 4,983,167 | 1/1991 | Sahota | 606/194 |
| 5,000,734 | 3/1991 | Boussignac et al. | 604/96 |
| 5,002,531 | 3/1991 | Bonzel | 604/96 |
| 5,015,231 | 5/1991 | Keith et al. | 604/96 |
| 5,019,042 | 5/1991 | Sahota | 604/101 |
| 5,049,131 | 9/1991 | Deuss | 604/96 |
| 5,053,007 | 10/1991 | Euteneuer | 604/96 |
| 5,066,298 | 11/1991 | Hess | 606/194 |
| 5,078,685 | 1/1992 | Colliver | 604/96 |
| 5,085,662 | 2/1992 | Willard | 606/159 |
| 5,090,958 | 2/1992 | Sahota | 604/98 |
| 5,108,370 | 4/1992 | Walinsky | 604/96 |
| 5,135,535 | 8/1992 | Kramer | 606/194 |
| 5,137,512 | 8/1992 | Burns et al. | 604/96 |
| 5,147,377 | 9/1992 | Sahota | 606/194 |
| 5,160,321 | 11/1992 | Sahota | 604/96 |
| 5,180,367 | 1/1993 | Kontos et al. | 604/101 |
| 5,232,446 | 8/1993 | Arney | 604/96 |
| 5,267,958 | 12/1993 | Buchbinder et al. | 604/96 |
| 5,281,203 | 1/1994 | Ressemann | 604/164 |
| 5,306,261 | 4/1994 | Alliger et al. | 604/280 |
| 5,318,532 | 6/1994 | Frassica | 604/96 |
| 5,320,605 | 6/1994 | Sahota | 604/101 |
| 5,328,472 | 7/1994 | Steinke et al. | 604/102 |
| 5,336,184 | 8/1994 | Teirstein | 604/102 |
| 5,338,300 | 8/1994 | Cox | 604/96 |
| 5,342,307 | 8/1994 | Euteneuer et al. | 604/103 |
| 5,352,236 | 10/1994 | Jung et al. | 606/194 |
| 5,364,376 | 11/1994 | Horzewski et al. | 604/280 |
| 5,368,567 | 11/1994 | Lee | 604/102 |
| 5,380,319 | 1/1995 | Saito et al. | 606/28 |

(List continued on next page.)

FOREIGN PATENT DOCUMENTS

| | | |
|---|---|---|
| 0 611 582 A2 | 8/1994 | European Pat. Off. . |
| WO 92/17236 | 10/1992 | WIPO . |
| WO 92/22345 | 12/1992 | WIPO . |
| WO 94/11048 | 5/1994 | WIPO . |
| WO 94/11053 | 5/1994 | WIPO . |

*Primary Examiner*—Wynn Wood Coggins
*Assistant Examiner*—Sharon Finkel
*Attorney, Agent, or Firm*—Crompton, Seager & Tufte, LLC.

[57] ABSTRACT

A convertible catheter assembly for performing an intravascular procedure incorporates a guide wire lumen having at least a proximal segment thereof manufactured from a collapsible tubular member. The catheter assembly includes a full length guide wire lumen and an intermediate guide wire port therein so that the catheter may be utilized in a single operator exchange or an over-the-wire mode. The collapsible proximal segment of the guide wire lumen decreases the overall profile of the catheter by collapsing radially inward when not in use during a single operator exchange procedure.

21 Claims, 2 Drawing Sheets

U.S. PATENT DOCUMENTS

| | | | |
|---|---|---|---|
| 5,383,890 | 1/1995 | Miraki et al. | 606/194 |
| 5,395,332 | 3/1995 | Ressemann et al. | 604/96 |
| 5,395,335 | 3/1995 | Jang | 604/102 |
| 5,409,458 | 4/1995 | Khairkhahan et al. | 604/96 |
| 5,417,707 | 5/1995 | Parkola | 606/194 |
| 5,425,710 | 6/1995 | Khair et al. | 604/96 |
| 5,443,456 | 8/1995 | Alliger et al. | 604/280 |
| 5,462,530 | 10/1995 | Jang | 604/160 |
| 5,466,222 | 11/1995 | Ressemann et al. | 604/96 |
| 5,489,271 | 2/1996 | Andersen | 604/102 |
| 5,520,647 | 5/1996 | Solar | 604/102 |
| 5,549,556 | 8/1996 | Ndondo-Lay et al. | 604/102 |
| 5,569,294 | 10/1996 | Parkola | 606/194 |
| 5,584,852 | 12/1996 | Parkola | 606/194 |
| 5,752,932 | 5/1998 | Ellis et al. | 604/96 |
| 5,846,259 | 12/1998 | Berthiaume | 606/192 |
| B1 4,762,129 | 7/1991 | Bonzel | 606/194 |

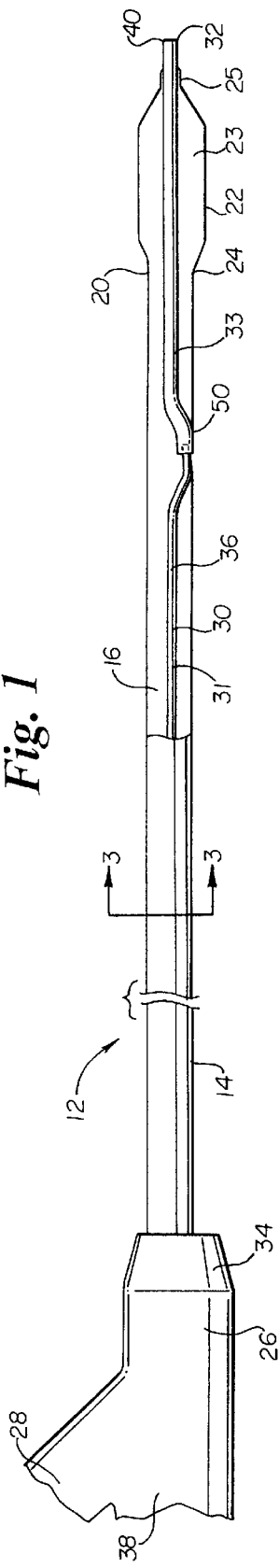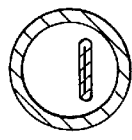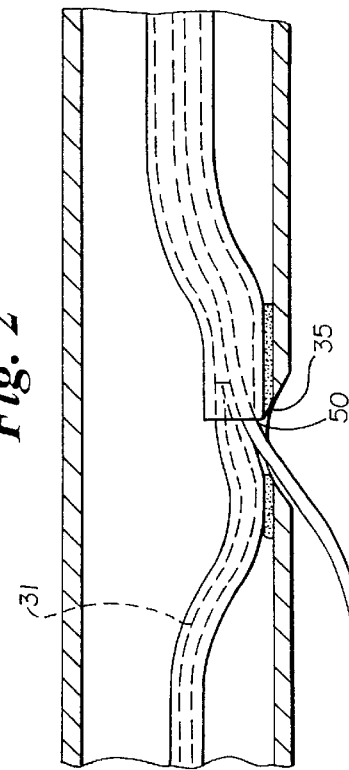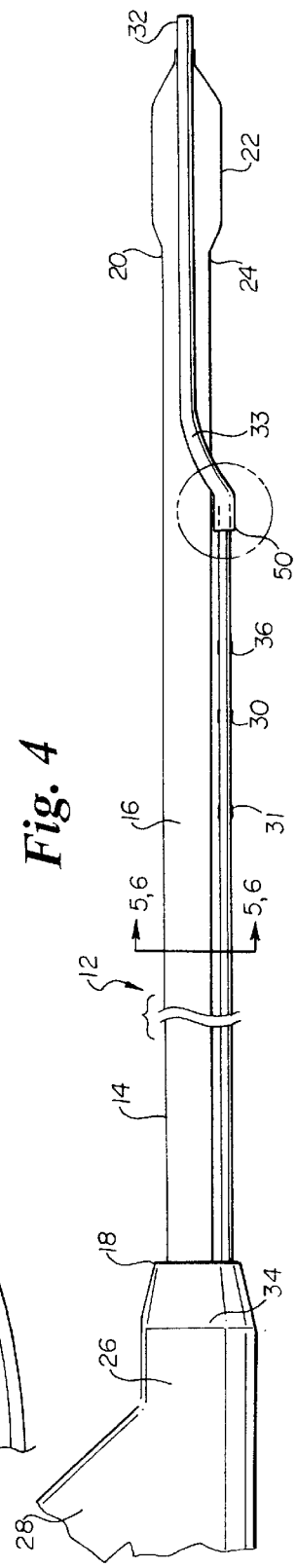

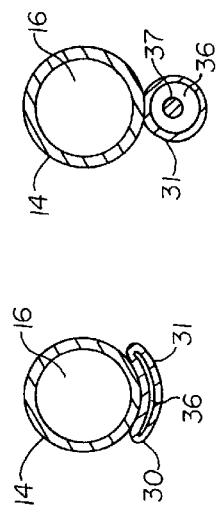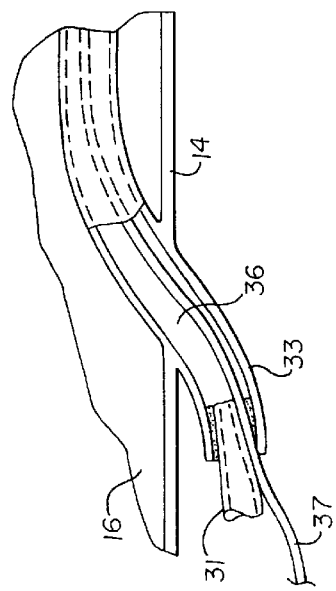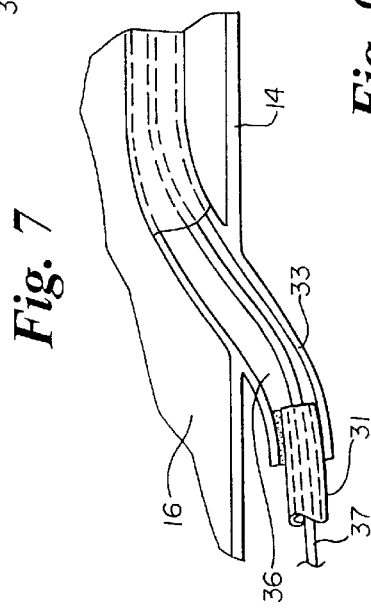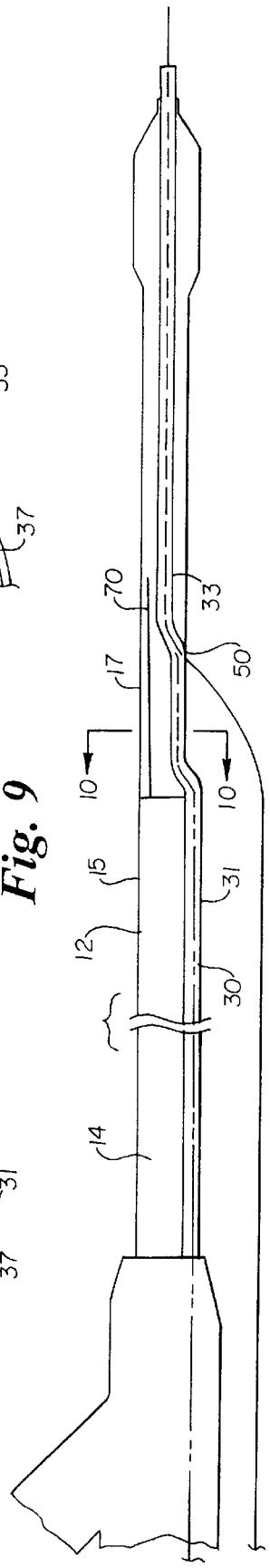

CONVERTIBLE CATHETER INCORPORATING A COLLAPSIBLE LUMEN

TECHNICAL FIELD

This invention relates to the field of intravascular medical devices used in combination with guide members. More specifically, the present invention relates to an intravascular balloon dilatation catheter incorporating both a full length and partial length guide wire lumen capability, wherein the proximal portion of the full length lumen is collapsible.

BACKGROUND OF THE INVENTION

Intravascular catheterization devices have proven to be useful and efficient for both therapeutic and diagnostic purposes. Intravascular therapeutic techniques, such as angioplasty, atherectomy, and laser irradiation, have been developed as alternatives to bypass surgery for treating vascular diseases or other conditions that occlude or reduce the lumen size of portions of a patient's vascular system. In particular, balloon angioplasty has proven to be a useful and in many circumstances a preferred treatment for obstructive coronary diseases. Also, intravascular diagnostic techniques, such as ultrasonic imaging and Doppler blood flow measurements, have been developed to measure or image the extent of an occlusion of a vessel (e.g., stenosis). The devices used to perform the aforementioned intravascular therapeutic and diagnostic techniques may be used together or in conjunction with more invasive techniques such as coronary surgery.

These intravascular therapeutic and diagnostic devices have achieved acceptance because of their effectiveness as well as the fact that they can be used in a minor surgical procedure that is relatively nondisruptive to the patient compared to coronary surgery. These devices rely on the positioning of a catheter into the vascular system of a patient via an incision at an accessible location which may be remote from the site of the occlusion or stenosis. For example, the accessible location may be the femoral artery at the groin. The intravascular device is then advanced through the incision via the femoral artery to a desired coronary distal site. The distal sites into which the device may be advanced include the coronary arteries, branch vessels stemming from the external carotid artery such as the occipital and the arteries leading to the vessels of the head and brain, splenic, and the inferior mesenteric and renal arteries leading to the organs of the thorax as well as other vessels.

Because of the small size of some of these vessels and the tortuous passages through the vessels, positioning of a catheter device through a patient's vasculature can be a difficult and time consuming task requiring considerable skill on the part of the physician. For example, in order to perform an angioplasty dilation, the angioplasty balloon catheter must be positioned across the stenosis in the arterial site. The stenosis may be located in a tortuous portion of the coronary vasculature and, furthermore, the obstructive arterial disease may impede crossing the stenosis with the balloon portion of the angioplasty catheter. Thus, not all arterial obstructions can be successfully treated by present intravascular balloon catheter procedures because some arterial obstructions are not readily accessible to a balloon dilation catheter. Accordingly, there is often a need for intravascular catheters of very low profile that can be positioned in narrow, tortuous regions of a person's vasculature.

Another important consideration relating to intravascular procedures, such as angioplasty, relates to the exchange of various devices used to perform the procedures. Intravascular therapeutic and diagnostic devices come in various types and sizes suitable for the vessel size and location in which the treatment is to be performed. Sometimes, it becomes necessary to exchange a first therapeutic device for one of a different size after an unsuccessful attempt has been made to position the first device in the appropriate location. It may also become necessary to exchange therapeutic devices after the first device is successfully positioned in the desired location. This may be necessitated because it becomes apparent that the first device is the wrong size or configuration, or because it is determined that additional therapeutic or diagnostic procedures with a different size or type of device is required.

Several different types of catheter constructions have been developed for positioning intravascular therapeutic or diagnostic catheters through a patient's vasculature. Two primary types of catheter constructions are the over-the-wire (OTW) type catheters and the single operator exchange (SOE) type catheters.

An over-the-wire type catheter, includes a central lumen through the entire length of the intravascular device that can accommodate a separate guide wire that is movable, and removable, in relation to the catheter to facilitate positioning the catheter in a remote vessel location over the guide wire. In the over-the-wire construction, the catheter typically includes a lumen adapted to receive the guide wire from a proximal end to the distal end of the device. The guide wire is initially loaded through the lumen of the over-the-wire catheter and extends out from the distal end thereof. Then, the guide wire and the intravascular catheter are advanced together and positioned in the vessel at the desired site. The guide wire may be advanced distally of the distal end of the catheter and steered, as necessary, to traverse tortuous passages of the vessel with the catheter subsequently advanced distally over the wire tracking the wires path. With the guide wire extending through the full length lumen, the guide wire provides some column support to the catheter shaft especially in the distal portion thereof. This improves the pushability of the catheter. The guide wire may then be withdrawn proximally through the lumen of the catheter or may be left in place extending from the distal end of the catheter during the procedure.

The over-the-wire type intravascular catheter facilitates exchanges because a first catheter can be exchanged with a second catheter without removing the guide wire. This allows an exchange of catheters without having to repeat the difficult and time-consuming task of positioning the guide wire. In order to leave the distal end of the guide wire in place, it is preferred to maintain a hold on a proximal end portion of the guide wire during the exchange operation. One way to maintain such a hold is to use a guide wire having a sufficiently long length (e.g., 300 cm) so that the entire catheter can be completely withdrawn over the guide wire while maintaining a hold on a portion of the wire. A disadvantage of this method is that the long proximally extending portion of the guide wire may be in the way during the procedure. Another way to maintain a hold on a portion of the guide wire during an exchange operation is to use a guide wire extension. A disadvantage of this method is that not all guide wires are adapted to connect to an extension wire, and moreover, the step of connecting the guide wire to the extension wire can sometimes be tedious and difficult to perform.

A second type of catheter, which facilitates the exchange of a first catheter with a second catheter, is the single-operator exchange type construction. With the single-operator exchange type construction, a guide wire occupies a position adjacent and exterior to the intravascular catheter along proximal and intermediate portions of the catheter and enters into a short guide wire lumen of the catheter via an opening at a location close to a distal portion of the catheter. With this type of construction, the catheter can be positioned in the patient's vessel by positioning a guide wire in the desired location and advancing the catheter device over the wire. An advantage of the short guide wire lumen is that in the event it becomes necessary to exchange the catheter, the position of the guide wire can be maintained during withdrawal of the catheter without the use of a long guide wire (e.g., 300 cm) or an extension wire. Because the proximal end of the guide wire is exterior to the proximal end of the catheter, the proximal end of the guide wire can be held during withdrawal of the catheter so that the position of the distal end of the guide wire in the patient's vessel can be maintained. With this type of catheter, it is necessary that the distance from the distal end of the catheter to the proximal guide wire lumen entrance is less than the length of the guide wire that extends proximally out of the patient.

Although single operator exchange catheters make it easier to exchange catheters, the construction has two disadvantages. First, the guide running external to the catheter shaft does not provide any column support for the shaft nor does the shaft provide support for the wire if the wire is pushed distally to cross a lesion. Second, with the single operator exchange design, the guide wire can not be replaced while the catheter remains in the body.

Just as it is sometimes necessary to exchange an intravascular catheter, it may also become necessary to exchange the guide wire or otherwise assist in advancing the guide wire to the desired location in the vessel. After the guide wire and catheter are in the vessel, it may be determined that the size or shape of the guide wire is inappropriate for advancement to the desired position in a vessel. For example, the diameter of the guide wire may be too large for advancement past an extensive stenosis or occlusion in a vessel or for advancement in another relatively small vessel. The diameter of the guide wire may also be too small for effective advancement of the guide wire and catheter to the desired location in the vessel.

It may also be determined that the shape or construction of the guide wire is inappropriate for advancement of the guide wire to the desired position after the guide wire and catheter are in the vessel. For example, a distal portion of the guide wire is often bent a desired amount prior to insertion into the body of a patient to allow manipulation of the guide wire through various vessels. After the guide wire is in a vessel, it may be determined that a guide wire with a different "bend" is necessary to advance further to the desired position in the vessel or to advance into another vessel. The distal tip of the guide wire may also acquire an inappropriate bend during advancement of the guide wire in the vessel. For example, the distal tip of the guide wire may prolapse when movement of the tip is impeded and the guide wire is advanced further in the vessel.

When it is determined that the configuration of the guide wire is inappropriate for advancement in the vessel, the guide wire is typically exchanged for a guide wire having the desired configuration. With an over-the-wire type catheter, the guide wire can be withdrawn through the lumen of the catheter and a second guide wire can be installed while leaving the catheter in position. However, with a single-operator exchange type catheter, a guide wire exchange cannot readily be performed without withdrawing the catheter. Once the distal end of the first guide wire is withdrawn proximally from the proximal guide wire lumen opening of the catheter, a second guide wire cannot readily be positioned in the proximal guide wire lumen opening without also withdrawing the catheter so that the proximal guide wire lumen opening is outside the body of a patient.

To derive the benefits achieved from use of an over-the-wire catheter and a single operator exchange catheter, while overcoming the deficiencies of each, Scopton et al. disclose a convertible catheter assembly which includes both an over-the-wire capability and a single operator exchange capability. The Scopton et al. disclosure is made in PCT application Ser. No. WO/17236, published on Oct. 15, 1992 and entitled "ADJUSTABLY STIFFENABLE CONVERTIBLE CATHETER ASSEMBLY". The disclosure of Scopton et al. is incorporated herein by reference. However, because the Scopton et al. design includes a separate proximal guide wire lumen and separate proximal inflation lumen, the overall profile of the catheter is larger than with a standard single operator exchange catheter which has only a single lumen in the proximal shaft portion. There is therefore a need in the art for a catheter design which incorporates the beneficial features of both a single operator exchange catheter and an over-the-wire catheter as discussed above, however, there is further a need for a design which reduces the overall profile of the catheter shaft by eliminating the profile increase created by two separate lumens over the entire length of the catheter assembly. The present catheter design reduces the overall profile of the catheter over a substantial portion length of the catheter by incorporating a collapsible lumen.

SUMMARY OF THE INVENTION

The present invention is directed to a convertible catheter assembly which is preferably utilized for performing an intravascular procedure such as a balloon dilatation of a stenosed region. As a convertible catheter, the present invention incorporates features which allow the catheter to be utilized in a first mode, which is an over-the-wire mode, and in a second mode, which is a single operator exchange mode by incorporating both a full length guide wire lumen and a short distal guide wire lumen. The short distal guide wire lumen is formed by including an additional intermediate guide wire port which is formed substantially distal of the proximal end of the catheter assembly so that a guide wire may enter through the intermediate guide wire port and extend out the distal end of the catheter to provide ease of catheter exchange if desired. The full length guide wire lumen provides the benefits of a standard over-the-wire catheter in that a guide wire may be extended through the entire length of the catheter to both provide column support to the catheter or guide wire and to allow for ease of exchange of guide wires if necessary during a procedure.

The present convertible catheter assembly provides a benefit over prior art devices in that the tubular member forming a proximal portion of the guide wire tube is designed to radially collapse inward when external force or pressure is applied to the outside thereof. The collapsible tube can be utilized to insert a guide wire when necessary. In preferred embodiments, the collapsible tubular member extends distally from the proximal end of the catheter to a point substantially distal thereof, but preferably terminating at about an intermediate guide wire port which is utilized for insertion of the guide wire in single operator exchange mode. The collapsible guide wire lumen allows for reducing the overall profile of the catheter shaft by eliminating the volume occupied by the cross section of the circular tubular member which would otherwise have to be utilized to provide a full-length guide wire lumen.

The catheter design of the present invention generally includes a first elongate tubular member having a proximal end and a distal end with a lumen extending therethrough. A second elongate tubular member having a proximal end and a distal end with a guide wire receiving lumen extending therethrough is coaxially disposed within the first elongate tubular member. The second elongate tubular member includes a proximal guide wire opening on the proximal end thereof and a distal guide wire opening on the distal end thereof. The second elongate tubular member includes a proximal segment and a distal segment with the proximal segment including a collapsible tubular member. The catheter also includes an inflatable balloon, which has a proximal end sealed to the first elongate tubular member proximate the distal end thereof, and a distal end sealed to the second elongate tubular member proximate the distal end thereof. The balloon defines an internal volume which is in fluid communication with the lumen of the first elongate member which is formed by the annular space between the first and second elongate tubular members. In this embodiment, when the balloon is pressurized through the lumen of the first elongate tubular member, the proximal segment of the second elongate tubular member collapses radially within the lumen to provide additional volume therein and reduce the pressure drop over the length of the first tubular member.

In a second alternative embodiment, the catheter of the present invention also includes a first elongate tubular member having a proximal end and a distal end with a lumen extending therethrough. A second elongate tubular member having a proximal end and a distal end with the guide wire receiving lumen extending therethrough includes a distal portion which is coaxially disposed within the first elongate tubular member lumen and a proximal portion which is disposed adjacent and external to the first elongate tubular member. The second elongate tubular member transitions from external and adjacent to the first elongate tubular member to internal and coaxial with the first elongate tubular member at a point substantially distal of the proximal end of the tubular members. The second tubular member passes through an opening into the first elongate tubular member lumen. As with the previous embodiment, the second elongate tubular member includes a proximal segment and a distal segment with the proximal segment including a collapsible tube, which, in use, collapses radially against the outside surface of the first elongate tubular member when the catheter is inserted to help reduce the overall profile of the catheter. If the catheter is to be operated in an over-the-wire mode, the guide wire can pass through the collapsible tube as necessary.

Each of the embodiments of the present invention include an intermediate guide wire port from outside the catheter body into the distal segment of the second elongate tubular member so that the catheter can be used in a single operator exchange mode. In a preferred embodiment, an opening is formed at the junction of the proximal segment with the distal segment of the second elongate tubular member. The collapsible tube is preferably partially inserted into the lumen of the distal segment such that the guide wire can be inserted therein by collapsing a portion of the wall of the collapsible tubular member.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 is a schematic drawing of a convertible catheter assembly having a full length inner coaxial guide wire lumen with an intermediate guide wire port formed therein, wherein the proximal portion of the guide wire lumen is collapsible radially;

FIG. 2 is a schematic cross section depicting an alternative intermediate guide wire port structure for the catheter of FIG. 1;

FIG. 3 is a cross-sectional view of FIG. 1 at line 3—3 depicting the proximal segment of the guide wire lumen collapsed during balloon inflation;

FIG. 4 is a schematic cross-sectional view of an alternative embodiment of the present invention, wherein the collapsible proximal portion of the guide wire tube is external and adjacent to the catheter body over a portion of the length thereof;

FIG. 5 is a cross-sectional view of the catheter of FIG. 4 at line 5—5 depicting a collapsible guide wire lumen in a collapsed state;

FIG. 6 is a cross-sectional view of the catheter of FIG. 4 at line 6—6 in an over-the-wire mode;

FIG. 7 is a partial cross-sectional detail of the full length guide wire lumen at the juncture between the collapsible proximal segment and non-collapsible distal segment with the guide wire inserted in an over-the-wire mode;

FIG. 8 is a detailed cross section similar to that of FIG. 7 except the guide wire is inserted in a single operator exchange mode;

FIG. 9 depicts an alternative embodiment of the present invention similar to that of FIG. 4, however, incorporating a dual lumen shaft portion; and FIG. 10 is a cross-sectional view of the catheter of FIG. 9 at line 10—10 depicting the dual lumen tubular structure.

DETAILED DESCRIPTION OF THE PREFERRED EMBODIMENT

Each of the embodiments of the catheter of the present invention are directed to a convertible catheter assembly for performing an intravascular procedure. By convertible catheter, it is meant that the catheter incorporates a full length guide wire lumen so that the catheter can be operated in an over-the-wire mode while also including an intermediate guide wire port which accesses the guide wire lumen at a point substantially distal from the proximal end of the catheter. By utilizing an intermediate guide wire port, a guide wire may be extended through the short lumen from the intermediate guide wire port to the distal end of the catheter. Thus, the catheter provides the benefits of an over-the-wire catheter, which include additional column support for the catheter or guide wire in crossing a lesion. The catheter also has the ability to readily exchange guide wires while in a single operator exchange mode without the use of a long guide wire or extension wire.

Each of the embodiments of the present invention described below incorporate both a first elongate tubular member and a second elongate tubular member. The second elongate tubular member in each embodiment provides a guide wire lumen throughout the length of the catheter. Also in each embodiment, the second elongate tubular member includes a proximal portion and a distal portion, with the proximal portion extending over a substantial portion of the length of the catheter. The collapsible tube, when exposed to pressure or force, collapses radially to a reduced profile cross section. The reduced profile of the collapsible tube allows making the catheter of the present invention of lower overall profile while maintaining inflation and deflation times at an optimum. The several embodiments of the present invention incorporate many like features, therefore, common features are assigned common reference numerals throughout the disclosure.

Referring now to FIG. 1, a schematic partial cross section of a first embodiment of the present convertible catheter assembly 12 incorporating the collapsible proximal guide wire lumen 31 is depicted. The convertible catheter assembly 12 includes a first elongate tubular member 14 having a lumen 16 extending therethrough. The first elongate tubular member 14 includes a proximal end 18 and a distal end 20.

The lumen 16 of the first elongate tubular member 14 is in fluid communication with an inflatable balloon 22 that has a proximal end 24 sealingly attached to the first elongate tubular member 14, proximate its distal end 20. In preferred embodiments, the proximal end 18 of the first elongate tubular member 14 has a hub assembly 26 attached thereto. The hub assembly provides an inflation port 28 for injection of inflation fluid into the proximal end 18 of the first elongate tubular member 14.

In preferred embodiments, the first elongate tubular member 14 is manufactured from a polymeric material such as high-density polyethylene. Although depicted as a single elongate tubular member, the first elongate tubular member 14 may be comprised of multiple segments which are secured generally end-to-end (using an adhesive lap joint or the like) to provide a continuous lumen 16 therethrough. For example, a proximal segment could be manufactured from a metallic hypotube such as stainless steel, with a polymeric distal section. The segments may be selected based on flexibility desired in the region of use along the axial length of the convertible catheter assembly 12.

The convertible catheter assembly 12 of FIG. 1 also includes a second elongate tubular member 30 having a distal end 32 and a proximal end 34 which is attached within the hub assembly 28 depicted in FIG. 1. The second elongate tubular member 30 has a guide wire receiving lumen 36 extending therethrough which includes a proximal guide wire opening 38 at the proximal end 34 and a distal guide wire opening 40 at the distal end 32 of the second elongate tubular member 30. The second elongate tubular member 30 is generally coaxially disposed within the lumen 16 of the first elongate tubular member 14 over the length of the first elongate tubular member 14. The second elongate tubular member 30 extends distally beyond the distal end 20 of the first elongate tubular member 14. The distal end 25 of the balloon 22 is sealingly attached to the second tubular member 30 proximate its distal end 32. As attached, the balloon 22 defines an internal volume 23 in fluid communication with the lumen 16 of the first tubular member 14.

As described thus far, the catheter assembly 12 of the present invention comprises a standard over-the-wire catheter. To provide a convertible capability, so that the catheter assembly 12 can be utilized as a single operator exchange catheter, an intermediate guide wire port 50 is provided through the wall of the first elongate tubular member 14 and through the wall of the second elongate tubular member 30 into the guide wire receiving lumen 36. The intermediate guide wire port 50 is preferably located at an axial location substantially distal of the proximal end of the elongate tubular members.

In a preferred embodiment, as depicted in FIG. 1, the intermediate guide wire port is formed at the desired axial location by drawing the second tubular member 30 in a desired region over to and against the interior wall of the first tubular member 14. It is preferred that the outside surface of the second elongate tubular member be secured to the interior wall of the first elongate tubular member to form a secured region with the walls in contact with each other. The second elongate tubular member 30 can be secured utilizing an adhesive, or alternatively, thermally bonded. By forming the secured region, the intermediate guide wire port 50 can readily be formed through both walls while maintaining sealed separation from the inflation lumen 16 of the first elongate tubular member 14.

The second elongate tubular member 30 includes a proximal portion 31 and a distal portion 33. The two portions are joined to form a single lumen extending therethrough. As depicted in FIG. 1, the preferred junction between the proximal portion 31 of the second elongate tubular member 30 and the distal portion 33 of the second elongate tubular member is proximate the intermediate guide wire port 50, preferably just proximal thereto. The proximal portion 31 is a collapsible tube, which radially compresses or collapses when subjected to inflation fluid pressure sufficient to inflate the balloon member 22. The proximal and distal portions can be joined by inserting the proximal portion 31 into the lumen of the distal portion and securing with an adhesive or thermal bond. The distal portion 33 is preferably manufactured from a non-collapsible tubular member which is sufficiently rigid to be secured to the interior wall of the first elongate tubular member 14 and form the intermediate guide wire port 50 therethrough. The collapsible tube is preferably manufactured from an elastomeric polymer which collapses radially under pressure, yet regains its open lumen therethrough when the external force or pressure ceases. Under either state, a guide wire can be slidably received in the lumen of the collapsible tubular member.

Referring now to FIG. 2, a schematic cross-sectional detail of the area of attachment of the second elongate tubular member 30 to the wall of the first elongate tubular member 14 in an alternative embodiment is disclosed. In this embodiment, the intermediate guide wire port 50 is formed into the proximal end 35 of the distal segment 33 with the guide wire insertable by deflecting a portion of the wall of the collapsible proximal segment 31. The structure provides a gate which prevents the guide wire from coming out the intermediate guide wire port 50 when it is threaded from the proximal end of the catheter to the distal end in an over-the-wire mode.

Referring now to FIG. 3, a cross section of the catheter assembly 12 at line 3—3 in FIG. 1 is depicted. As depicted, the proximal portion 31 of the second elongate tubular member 30 is shown in a collapsed state as when the balloon 22 is inflated. As readily seen in the cross section, the overall cross-sectional area available for inflation fluid flow is increased due to the collapsed configuration of the second elongate tubular member 30 therein. This configuration allows for utilizing a smaller diameter first elongate tubular member while maintaining optimum inflation and deflation times. This reduces the overall profile of the catheter so that it may be utilized to access smaller vascular lumens.

Referring now to FIG. 4, an alternative embodiment of the convertible catheter assembly 12 of the present invention is depicted schematically. The embodiment of FIG. 4 is similar to that disclosed in FIG. 1, having many common features which are identified with like reference numerals.

As with the embodiment of FIG. 1, the embodiment of FIG. 4 includes a first elongate tubular member 14 having a proximal end 18 and a distal end 20 with a lumen 16 extending therethrough. A balloon 22 has a proximal end 24 sealingly connected proximate the distal end 20 of the first elongate tubular member 14. The proximal end 18 of the first elongate tubular member 14 has a hub 26 connected thereto, which provides access via an inflation port 28 to the lumen 16 from outside the proximal end of the catheter assembly 12.

The embodiment of FIG. 4 also includes a second elongate tubular member 30 which has a proximal end 34 and a distal end 32 with a guide wire receiving lumen 36 extending therethrough. The proximal end includes a proximal guide wire opening and the distal end includes a distal guide wire opening on the distal end of the catheter.

The second elongate tubular member 30 includes a proximal segment 31 and a distal segment 33, as with the embodiment of FIG. 1. However, the embodiment of FIG. 4 includes a second elongate tubular member 30 having a distal portion 33 coaxially disposed within the first elongate tubular member 14 and a proximal portion 31 disposed adjacent and external to the first elongate tubular member 14, with the second elongate tubular member 30 transitioning from external and adjacent of the first elongate tubular member 14 to internal and coaxially with the first elongate tubular member 14 at a point substantially distal on the tubular members. The transition occurs through an opening into the first elongate tubular member 14 lumen 16. As would be understood by one of skill in the art, the point of penetration through the tubular wall must be sealed around the outside of the second elongate tubular member 30 extending therethrough to prevent the leakage of inflation fluid during use.

Now referring to FIGS. 5 and 6, cross sections of the catheter assembly 12 at line 5—5 and 6—6 are depicted showing the function of the proximal portion 31 of the second elongate tubular member 30 in use as a single operator exchange device and as a standard over-the-wire device. The proximal segment 31 of the second elongate tubular member 30 is at least partially, over the length thereof, manufactured from a collapsible tubular member. As depicted in FIG. 5, when the catheter is used in single operator exchange mode so that there is not a guide wire extending through the guide wire lumen 36, the collapsible tubular member 31 will compress radially when a force is exerted on the outside surface of the tube, as for example, when inserted in the body and contacting a vessel wall or guide catheter wall. This, of course, reduces the overall profile of the catheter assembly 12.

Now referring to FIG. 6, the same cross section as FIG. 5 is depicted when the catheter assembly 12 is utilized in a standard over-the-wire mode with a guide wire 37 extending through the proximal section 31 of the second elongate member lumen 36.

In a preferred embodiment of the catheter assembly of FIG. 4, the proximal segment 31 of the second elongate member 30 is joined to the distal segment 33 proximate the intermediate guide wire port 50. As depicted in FIG. 4, the proximal segment 31 is preferably inserted within the lumen of the distal segment. The joint between these two portions of the second elongate tubular member 30, in a preferred embodiment, is depicted in FIGS. 7 and 8 showing the detail of that which is depicted in the circular area of FIG. 4. FIG. 7 depicts the catheter assembly operating in an over-the-wire mode and FIG. 8 depicts the catheter operating a single operator exchange mode. As shown in FIG. 7, the proximal segment 31 is inserted within the lumen of the distal segment 33 and adhesively bonded therein. With such design, the guide wire 37 can extend through the entire length of the catheter assembly. FIG. 7 also depicts the way the distal segment 33 of the second elongate tubular member penetrates the wall of the first elongate tubular member 14 so that it may run coaxially within the lumen 16 to the distal end of the catheter 32.

FIG. 8 depicts the detail of FIG. 7 when the catheter assembly 12 is operated in a single operator exchange mode. The proximal segment 31 of the second elongate tubular member is preferably adhesively bonded over only a portion of the exterior surface of the proximal tubular member 31. Because the proximal segment 31 is manufactured from a collapsible tubular member, the portion which is not adhesively bonded can readily be indented or compressed radially inward along the one side as indicated so that a guide wire may be slidably received in a single operator exchange mode through the intersection of the tubular members. Alternatively, a hole could be provided in the distal segment 33 of the second elongate tubular member to provide access to the guide wire lumen 36.

Referring now to FIGS. 9 and 10, another alternative embodiment of the present convertible catheter assembly 12 is depicted. The embodiment of FIGS. 9 and 10 is similar to that discussed above with respect to FIGS. 4–8. Therefore, only the differences between the embodiments are discussed herein. In particular, the second elongate tubular member 30 includes a proximal segment 31 which is collapsible and a distal segment 33 which is generally not collapsible in use. The proximal segment or at least a portion of the proximal segment runs exterior and adjacent to the first elongate tubular member 14. As with the depictions in FIGS. 5 and 6, this portion of the second elongate tubular member 30 will collapse in the same manner when an external force is applied thereto. The distinction between the embodiment of FIGS. 4–8 and that depicted in FIGS. 9 and 10 is that an intermediate dual lumen segment is included in the catheter assembly. The dual lumen segment is depicted in cross section in FIG. 10. Thus, the first elongate tubular member 14 in this embodiment includes a proximal segment 15 and a distal segment 17 with the proximal segment being a single lumen portion and the distal segment including at least a portion which is dual lumen. The intermediate guide wire port 50 can be included by a port through the wall of the dual lumen section which allows access for a guide wire as indicated.

The embodiment of FIG. 9 further depicts a core wire 70 which extends distally from the proximal segment 15 of the first elongate tubular member. The core wire is particularly useful if there is a change in materials from the proximal segment 15 to the distal segment 17 to prevent kinking in that area. In a preferred embodiment, the proximal segment of the first elongate tubular member 14 is manufactured from a stainless steel or other metallic hypotube. The distal segment 17 is preferably manufactured from a polymeric material.

Numerous advantages of the invention covered by this documents have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A convertible catheter assembly for performing an intravascular procedure comprising:

(a) a first elongate tubular member having a proximal end and a distal end with a lumen extending therethrough;

(b) a second elongate tubular member having a proximal end and a distal end with a guide wire receiving lumen extending therethrough with a proximal guide wire opening on the proximal end thereof and a distal guide wire opening on the distal end thereof, said second elongate tubular member coaxially disposed within said first elongate tubular member, said second elongate tubular member including a proximal segment and a distal segment, said proximal segment including a collapsible tube;

(c) an inflatable balloon having a proximal end sealed to said first elongate tubular member proximate the distal end thereof and a distal end sealed to said second elongate tubular member proximate the distal end thereof, said balloon defining an internal volume therein in fluid communication with said lumen of said first elongate tubular member, wherein when said balloon is pressurized, said proximal segment of said second elongate tubular member collapses radially within said lumen of said first elongate tubular member; and, (d) an intermediate guide wire opening through the wall of said distal segment of said second elongate tubular member and the wall of said first elongate tubular member at a point substantially distal of the proximal end of said elongate tubular members, said opening configured for receiving a guide wire therethrough.

2. The convertible catheter assembly of claim 1, wherein said first elongate tubular member comprises a plurality of segments joined end to end to form a tubular member having a coextensive single lumen therethrough.

3. The convertible catheter assembly of claim 1, further comprising a core wire fixed within said first elongate tubular member at an intermediate point therein and extending distally therefrom.

4. The convertible catheter assembly of claim 1, wherein said proximal segment of said second elongate tubular member is a collapsible tube and said distal segment of said second elongate tubular member is non-collapsible in use.

5. The convertible catheter assembly of claim 4, wherein said proximal segment of said second elongate tubular member is manufactured from an elastic polymer.

6. The convertible catheter assembly of claim 1, wherein said first elongate tubular member includes a proximal hypotube segment and a distal polymer segment.

7. The convertible catheter assembly of claim 6, wherein said intermediate guide wire opening extends through the wall of said distal polymer segment into said distal segment of said second elongate tubular member.

8. A convertible catheter assembly for performing an intravascular procedure comprising:

(a) a first elongate tubular member having a proximal end and a distal end with a lumen extending therethrough;

(b) a second elongate tubular member having a proximal end and a distal end with a guide wire receiving lumen extending therethrough including a proximal guide wire opening on the proximal end thereof and a distal guide wire opening on the distal end thereof, said second elongate tubular member having a distal portion coaxially disposed within said first elongate tubular member and a proximal portion disposed adjacent and external to said first elongate tubular member with said second elongate tubular member transitioning from external and adjacent of said first elongate tubular member to internal and coaxial with said first elongate tubular member at a point substantially distal on said tubular members through an opening into said first elongate tubular member, said second elongate tubular member including a proximal segment and a distal segment, said proximal segment including a collapsible tube wherein when said catheter is inserted during use said proximal segment of collapses radially against the outside surface of said first elongate tubular member to reduce the overall profile of the catheter;

(c) an inflatable balloon having a proximal end sealed to said first elongate tubular member proximate the distal end thereof and a distal end sealed to said second elongate tubular member proximate the distal end thereof, said balloon defining an internal volume therein in fluid communication with said lumen of said first elongate tubular member;

(d) an intermediate guide wire opening into the distal segment of said second elongate tubular member, said opening configured for receiving a guide wire therethrough.

9. The convertible catheter assembly of claim 8, wherein said first elongate tubular member comprises a plurality of segments joined end to end to form a tubular member having a coextensive single lumen therethrough.

10. The convertible catheter assembly of claim 8, further comprising a core wire fixed within said first elongate tubular member at an intermediate point therein and extending distally therefrom.

11. The convertible catheter assembly of claim 8, wherein said proximal segment of said second elongate tubular member is a collapsible tube and said distal segment of said second elongate tubular member is non-collapsible in use.

12. The convertible catheter assembly of claim 11, wherein said proximal segment of said second elongate tubular member is manufactured from an elastic polymer.

13. The convertible catheter assembly of claim 8, wherein said first elongate tubular member includes a proximal hypotube segment and a distal polymer segment.

14. The convertible catheter assembly of claim 13, wherein said intermediate guide wire opening extends through the wall of said distal polymer segment into said distal segment of said second elongate tubular member.

15. A convertible catheter assembly for performing an intravascular procedure comprising:

(a) a first elongate tubular member having a proximal end and a distal end with a lumen extending therethrough;

(b) a second elongate tubular member having a proximal end and a distal end with a guide wire receiving lumen extending therethrough including a proximal guide wire opening on the proximal end thereof and a distal guide wire opening on the distal end thereof, said second elongate tubular member having a distal portion coaxially disposed within said first elongate tubular member and a proximal portion disposed adjacent and external to said first elongate tubular member with said second elongate tubular member transitioning from external and adjacent to said first elongate tubular member to internal and coaxial with said first elongate tubular member at a point substantially distal on said tubular members through an opening into said first elongate tubular member, said second elongate tubular member including a proximal segment and a distal segment, said proximal segment including a collapsible tube wherein when said catheter is inserted during use said proximal segment collapses radially against the outside surface of said first elongate tubular member to reduce the overall profile of the catheter;

(c) an inflatable balloon having a proximal end sealed to said first elongate tubular member proximate the distal end thereof and a distal end sealed to said second elongate tubular member proximate the distal end thereof, said balloon defining an internal volume therein in fluid communication with said lumen of said first elongate tubular member;

(d) an intermediate guide wire opening into the distal segment of said second elongate tubular member, said opening formed at the junction of said proximal segment and said distal segment wherein said collapsible tube is partially inserted into the lumen of said distal segment such that said guide wire can also be inserted therein by collapsing said tube as inserted into said lumen.

16. The convertible catheter assembly of claim 15, wherein said first elongate tubular member comprises a plurality of segments joined end to end to form a tubular member having a coextensive single lumen therethrough.

17. The convertible catheter assembly of claim 15, further comprising a core wire fixed within said first elongate tubular member at an intermediate point therein and extending distally therefrom.

18. The convertible catheter assembly of claim 15, wherein said proximal segment of said second elongate tubular member is a collapsible tube and said distal segment of said second elongate tubular member is non-collapsible in use.

19. The convertible catheter assembly of claim 18, wherein said proximal segment of said second elongate tubular member is manufactured from an elastic polymer.

20. The convertible catheter assembly of claim 15, wherein said first elongate tubular member includes a proximal hypotube segment and a distal polymer segment.

21. The convertible catheter assembly of claim 20, wherein said intermediate guide wire opening extends through the wall of said distal polymer segment into said distal segment of said second elongate tubular member.

* * * * *